United States Patent [19]

Rasmussen et al.

[11] Patent Number: 5,312,736
[45] Date of Patent: May 17, 1994

[54] ANTICOAGULANT ANALOGUES OF THE TISSUE FACTOR EXTRINSIC PATHWAY INHIBITOR (EPI) WITH REDUCED AFFINITY FOR HEPARIN

[75] Inventors: Jesper S. Rasmussen, Vanloese; Ole J. Nordfang, Hilleroed, both of Denmark

[73] Assignee: Novo Nordisk A/S, Bagsvaerd, Denmark

[21] Appl. No.: 828,920
[22] PCT Filed: Aug. 17, 1990
[86] PCT No.: PCT/DK90/00212
§ 371 Date: Jan. 27, 1992
§ 102(e) Date: Jan. 27, 1992
[87] PCT Pub. No.: WO91/02753
PCT Pub. Date: Mar. 7, 1991

[30] Foreign Application Priority Data

Aug. 18, 1989 [DK] Denmark ............... 4080/89

[51] Int. Cl.$^5$ ............... C07K 13/00; C12N 15/15; A61K 37/64
[52] U.S. Cl. ............... 435/69.2; 435/240.2; 435/252.3; 435/320.1; 536/23.5; 530/350; 530/380; 530/395; 514/8
[58] Field of Search ............... 530/350, 380, 384, 395; 536/23.1, 23.5; 435/69.2, 240.2, 252.3-252.35, 320.1; 514/8

[56] References Cited

U.S. PATENT DOCUMENTS 5,106,833 4/1992 Broze, Jr. et al. ............... 514/12

FOREIGN PATENT DOCUMENTS 0300988 1/1989 European Pat. Off.
0318451 5/1989 European Pat. Off.

OTHER PUBLICATIONS

Girard et al., Nature, vol. 338, pp. 518-520 (1989).
Warn-Cramer et al., Thrombosis Research, vol. 48, pp. 11-22 (1987).
Broze, Jr. et al., Proc. Natl. Acad. Sci. USA, vol. 84, pp. 1886-1890 (1987).
Wun, T.-C., et al. (1988) J. Biol. Chem. 263: 6001-04.
Broze, G. J., Jr., et al. (1990) Biochemistry 29: 7539-46.

Primary Examiner—Robert J. Hill, Jr.
Assistant Examiner—David L. Fitzgerald
Attorney, Agent, or Firm—Steve T. Zelson; Karen A. Lowney

[57] ABSTRACT

Novel extrinsic pathway inhibitors (EPI) are provided wherein one or more of the amino acid residues of native EPI have been deleted. A preferred group of the novel EPI analogues have no or a low heparin binding capacity. The novel EPI analogues can be used for the treatment of patients having coagulation disorders or cancer.

9 Claims, 12 Drawing Sheets

```
Asp Ser Glu Glu Asp Glu Glu His Thr Ile Ile Thr Asp Thr Glu Leu
 1           5               10                  15
Pro Pro Leu Lys Leu Met His Ser Phe Cys Ala Phe Lys Ala Asp Asp
             20              25              30
Gly Pro Cys Lys Ala Ile Met Lys Arg Phe Phe Phe Asn Ile Phe Tyr
         35              40                  45
Arg Gln Cys Glu Glu Phe Ile Tyr Gly Gly Cys Glu Gly Asn Gln Asn
     50              55              60
Arg Phe Glu Ser Leu Glu Glu Cys Lys Lys Met Cys Thr Arg Asp Asn
 65              70              75                  80
Ala Asn Arg Ile Ile Lys Thr Thr Leu Gln Gln Glu Lys Pro Asp Phe
             85              90              95
Cys Phe Leu Glu Glu Asp Pro Gly Ile Cys Arg Gly Tyr Ile Thr Arg
            100             105             110
Tyr Phe Tyr Asn Asn Gln Thr Lys Gln Cys Glu Arg Phe Lys Tyr Gly
         115             120             125
Gly Cys Leu Gly Asn Met Asn Asn Phe Glu Thr Leu Glu Glu Cys Lys
        130             135             140
Asn Ile Cys Glu Asp Gly Pro Asn Gly Phe Gln Val Asp Asn Tyr Gly
145             150             155             160
Thr Gln Leu Asn Ala Val Asn Asn Ser Leu Thr Pro Gln Ser Thr Lys
            165             170             175
Val Pro Ser Leu Phe Glu Phe His Gly Pro Ser Trp Cys Leu Thr Pro
            180             185             190
Ala Asp Arg Gly Leu Cys Arg Ala Asn Glu Asn Arg Phe Tyr Tyr Asn
        195             200             205
Ser Val Ile Gly Lys Cys Arg Pro Phe Lys Tyr Ser Gly Cys Gly Gly
        210             215             220
Asn Glu Asn Asn Phe Thr Ser Lys Gln Glu Cys Leu Arg Ala Cys Lys
225             230             235             240
Lys Gly Phe Ile Gln Arg Ile Ser Lys Gly Gly Leu Ile Lys Thr Lys
            245             250             255
Arg Lys Arg Lys Lys Gln Arg Val Lys Ile Ala Tyr Glu Glu Ile Phe
        260             265             270
Val Lys Asn Met
        275
```

Fig. 2

```
GTCGACAGAG CTGAGATCCT ACAGGAGTCC AGGGCTGGAG AGAAAACCTC        50

TGCGAGGAAA GGGAAGGAGC AAGCCGTGAA TTTAAGGGAC GCTGTGAAGC       100

AATC ATG GAT GCA ATG AAG AGA GGG CTC TGC TGT GTG CTG CTG     143
     Met Asp Ala Met Lys Arg Gly Leu Cys Cys Val Leu Leu
     1               5                   10

CTG TGT GGA GCA GTC TTC GTT TCG CCC AGC CAG GAA ATC CAT      185
Leu Cys Gly Ala Val Phe Val Ser Pro Ser Gln Glu Ile His
    15              20                  25
                                              PstI
GCC CGA TTC AGA AGA GGA GCC AGA TCA ACA CTG CAG CAA GAA      227
Ala Arg Phe Arg Arg Gly Ala Arg Ser Thr Leu Gln Gln Glu
        30              35                  40
                        BamHI
AAG CCA GAT TTC TGC TTT TTG GAA GAG GAT CCT GGA ATA TGT      269
Lys Pro Asp Phe Cys Phe Leu Glu Glu Asp Pro Gly Ile Cys
            45              50                  55

CGA GGT TAT ATT ACC AGG TAT TTT TAT AAC AAT CAG ACA AAA      311
Arg Gly Tyr Ile Thr Arg Tyr Phe Tyr Asn Asn Gln Thr Lys
                60              65

CAG TGT GAA AGG TTC AAG TAT GGT GGA TGC CTG GGC AAT ATG      353
Gln Cys Glu Arg Phe Lys Tyr Gly Gly Cys Leu Gly Asn Met
70              75                  80

XhoI
AAC AAT TTT GAG ACA CTC GAG GAA TGC AAG AAC ATT TGT GAA      395
Asn Asn Phe Glu Thr Leu Glu Glu Cys Lys Asn Ile Cys Glu
    85              90                  95
                                            KnpI
GAT GGT CCG AAT GGT TTC CAG GTG GAT AAT TAT GGT ACC TGA      437
Asp Gly Pro Asn Gly Phe Gln Val Asp Asn Tyr Gly Thr End
        100             105                 110

BglII       BglII           BglII
AGATCTGAAT TCTGAAGATC TAGGCCTATG AAGATCT                     474
```

Fig. 7

```
SalI
GTCGACAGAG CTGAGATCCT ACAGGAGTCC AGGGCTGGAG AGAAAACCTC          50

TGCGAGGAAA GGGAAGGAGC AAGCCGTGAA TTTAAGGGAC GCTGTGAAGC         100

AATC ATG GAT GCA ATG AAG AGA GGG CTC TGC TGT GTG CTG CTG       143
     Met Asp Ala Met Lys Arg Gly Leu Cys Cys Val Leu Leu
      1           5                      10

CTG TGT GGA GCA GTC TTC GTT TCG CCC AGC CAG GAA ATC CAT        185
Leu Cys Gly Ala Val Phe Val Ser Pro Ser Gln Glu Ile His
    15              20                      25

SacI
GCC CGA TTC AGA AGA GGA GCC AGA TCA GAG CTC CCA CCA CTG        227
Ala Arg Phe Arg Arg Gly Ala Arg Ser Glu Leu Pro Pro Leu
        30              35                  40

ApaI
AAA CTT ATG CAT TCA TTT TGT GCA TTC AAG GCG GAT GAT GGG        269
Lys Leu Met His Ser Phe Cys Ala Phe Lys Ala Asp Asp Gly
            45              50                  55

CCC TGT AAA GCA ATC ATG AAA AGA TTT TTC TTC AAT ATT TTC        311
Pro Cys Lys Ala Ile Met Lys Arg Phe Phe Phe Asn Ile Phe
                60              65

ACT CGA CAG TGC GAA GAA TTT ATA TAT GGG GGA TGT GAA GGA        353
Thr Arg Gln Cys Glu Glu Phe Ile Tyr Gly Gly Cys Glu Gly
70              75                      80

ClaI
AAT CAG AAT CGA TTT GAA AGT CTG GAA GAG TGC AAA AAA ATG        395
Asn Gln Asn Arg Phe Glu Ser Leu Glu Glu Cys Lys Lys Met
    85              90                      95

PstI
TGT ACA AGA GAT AAT GCA AAC AGG ATT ATA AAG ACA ACA CTG        437
Cys Thr Arg Asp Asn Ala Asn Arg Ile Ile Lys Thr Thr Leu
        100             105                 110

BamHI
CAG CAA GAA AAG CCA GAT TTC TGC TTT TTG GAA GAG GAT CCT        479
Gln Gln Glu Lys Pro Asp Phe Cys Phe Leu Glu Glu Asp Pro
            115             120                 125

GGA ATA TGT CGA GGT TAT ATT ACC AGG TAT TTT TAT AAC AAT        521
Gly Ile Cys Arg Gly Tyr Ile Thr Arg Tyr Phe Tyr Asn Asn
                130             135
```

Fig. 8 A

```
CAG ACA AAA CAG TGT GAA AGG TTC AAG TAT GGT GGA TGC CTG           563
Gln Thr Lys Gln Cys Glu Arg Phe Lys Tyr Gly Gly Cys Leu
140             145                 150

XhoI
GGC AAT ATG AAC AAT TTT GAG ACA CTC GAG GAA TGC AAG AAC           605
Gly Asn Met Asn Asn Phe Glu Thr Leu Glu Glu Cys Lys Asn
    155                 160                 165

ATT TGT GAA GAT GGT CCG AAT GGT TTC CAG GTG GAT AAT TAT           647
Ile Cys Glu Asp Gly Pro Asn Gly Phe Gln Val Asp Asn Tyr
        170                 175                 180

KpnI            BglII       BglII               BglII
GGT ACC TGA AGATCTGAAT TCTGAAGATC TAGGCCTATG AAGATCT              693
Gly Thr End
```

Fig. 8 B

```
SalI
GTCGACC ATG ATT TAC ACA ATG AAG AAA GTA CAT GCA CTT TGG         43
        Met Ile Tyr Thr Met Lys Lys Val His Ala Leu Trp
         1           5                   10

GCT AGC GTA TGC CTG CTG CTT AAT CTT GCC CCT GCC CCT CTT         85
Ala Ser Val Cys Leu Leu Leu Asn Leu Ala Pro Ala Pro Leu
        15                  20                  25

AAT CGT GAT TCT GAG GAA GAT GAA GAA CAC ACA ATT ATC ACA         127
Asn Ala Asp Ser Glu Glu Asp Glu Glu His Thr Ile Ile Thr
            30                  35                  40

GAT ACG GAG CTC CCA CCA CTG AAA CTT ATG CAT TCA TTT TGT         169
Asp Thr Glu Leu Pro Pro Leu Lys Leu Met His Ser Phe Cys
                45                  50

GCA TTC AAG GCG GAT GAT GGG CCC TGT AAA GCA ATC ATG AAA         211
Ala Phe Lys Ala Asp Asp Gly Pro Cys Lys Ala Ile Met Lys
55                  60                  65

AGA TTT TTC TTC AAT ATT TTC ACT CGA CAG TGC GAA GAA TTT         253
Arg Phe Phe Phe Asn Ile Phe Thr Arg Gln Cys Glu Glu Phe
    70                  75                  80

ClaI
ATA TAT GGG GGA TGT GAA GGA AAT CAG AAT CGA TTT GAA AGT         295
Ile Tyr Gly Gly Cys Glu Gly Asn Gln Asn Arg Phe Glu Ser
        85                  90                  95

CTG GAA GAG TGC AAA AAA ATG TGT ACA AGA GAT AAT GCA AAC         337
Leu Glu Glu Cys Lys Lys Met Cys Thr Arg Asp Asn Ala Asn
                100                 105

AGG ATT ATA AAG ACA ACA CTG CAG CAA GAA AAG CCA GAT TTC         379
Arg Ile Ile Lys Thr Thr Leu Gln Gln Glu Lys Pro Asp Phe
110                 115                 120

BamHI
TGC TTT TTG GAA GAG GAT CCT GGA ATA TGT CGA GGT TAT ATT         421
Cys Phe Leu Glu Glu Asp Pro Gly Ile Cys Arg Gly Tyr Ile
    125                 130                 135

ACC AGG TAT TTT TAT AAC AAT CAG ACA AAA CAG TGT GAA AGG         463
Thr Arg Tyr Phe Tyr Asn Asn Gln Thr Lys Gln Cys Glu Arg
        140                 145                 150

TTC AAG TAT GGT GGA TGC CTG GGC AAT ATG AAC AAT TTT GAG         505
Phe Lys Tyr Gly Gly Cys Leu Gly Asn Met Asn Asn Phe Glu
                155                 160                 165
```

Fig. 10 A

```
AGA CTC GAG GAA TGC AAG AAC ATT TGT GAA GAT GGT CCG AAT                547
Thr Leu Glu Glu Cys Lys Asn Ile Cys Glu Asp Gly Pro Asn
                170             175

BglII
GGT TTC CAG GTG GAT AAT TAT GGT ACC TGA AGATCTGAAT                      587
Gly Phe Gln Val Asp Asn Tyr Gly Thr End
180             185

BglII              BglII
TCTGAAGATC TAGGCCTATG AAGATCT                                           614
```

Fig. 10 B

SEQUENCE LISTING ( 1 ) GENERAL INFORMATION:

( i i i ) NUMBER OF SEQUENCES: 7

(2) INFORMATION FOR SEQ ID NO: 1:

(i) SEQUENCE CHARACTERISTICS:
        (A) LENGTH: 276 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (ix) FEATURE:
        (A) NAME/KEY: Protein
        (B) LOCATION: 1..276

(xi) SEQUENCE DESCRIPTION: SEQ ID NO: 1:

```
Asp Ser Glu Glu Asp Glu Glu His Thr Ile Ile Thr Asp Thr Glu Leu
 1               5                  10                  15

Pro Pro Leu Lys Leu Met His Ser Phe Cys Ala Phe Lys Ala Asp Asp
             20                  25                  30

Gly Pro Cys Lys Ala Ile Met Lys Arg Phe Phe Phe Asn Ile Phe Tyr
             35                  40                  45

Arg Gln Cys Glu Glu Phe Ile Tyr Gly Gly Cys Glu Gly Asn Gln Asn
 50                      55                  60

Arg Phe Glu Ser Leu Glu Glu Cys Lys Lys Met Cys Thr Arg Asp Asn
 65                  70                  75                  80

Ala Asn Arg Ile Ile Lys Thr Thr Leu Gln Gln Glu Lys Pro Asp Phe
                 85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
            195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
            275
```

(2) INFORMATION FOR SEQ ID NO: 2:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (i i) MOLECULE TYPE: cDNA (i x) FEATURE:
    (A) NAME/KEY: CDS
    (B) LOCATION: 105..437

(x i) SEQUENCE DESCRIPTION: SEQ ID NO: 2:

```
GTCGACAGAG CTGAGATCCT ACAGGAGTCC AGGGCTGGAG AGAAAACCTC TGCGAGGAAA      60

GGGAAGGAGC AAGCCGTGAA TTTAAGGGAC GCTGTGAAGC AATC ATG GAT GCA ATG     116
                                                 Met Asp Ala Met
                                                  1

AAG AGA GGG CTC TGC TGT GTG CTG CTG CTG TGT GGA GCA GTC TTC GTT      164
Lys Arg Gly Leu Cys Cys Val Leu Leu Leu Cys Gly Ala Val Phe Val
  5              10                  15                  20

TCG CCC AGC CAG GAA ATC CAT GCC CGA TTC AGA AGA GGA GCC AGA TCA      212
Ser Pro Ser Gln Glu Ile His Ala Arg Phe Arg Arg Gly Ala Arg Ser
             25                  30                  35

ACA CTG CAG CAA GAA AAG CCA GAT TTC TGC TTT TTG GAA GAG GAT CCT      260
Thr Leu Gln Gln Glu Lys Pro Asp Phe Cys Phe Leu Glu Glu Asp Pro
         40                  45                  50

GGA ATA TGT CGA GGT TAT ATT ACC AGG TAT TTT TAT AAC AAT CAG ACA      308
Gly Ile Cys Arg Gly Tyr Ile Thr Arg Tyr Phe Tyr Asn Asn Gln Thr
     55                  60                  65

AAA CAG TGT GAA AGG TTC AAG TAT GGT GGA TGC CTG GGC AAT ATG AAC      356
Lys Gln Cys Glu Arg Phe Lys Tyr Gly Gly Cys Leu Gly Asn Met Asn
 70                  75                  80

AAT TTT GAG ACA CTC GAG GAA TGC AAG AAC ATT TGT GAA GAT GGT CCG      404
Asn Phe Glu Thr Leu Glu Glu Cys Lys Asn Ile Cys Glu Asp Gly Pro
 85                  90                  95                 100

AAT GGT TTC CAG GTG GAT AAT TAT GGT ACC TGAAGATCTG AATTCTGAAG        454
Asn Gly Phe Gln Val Asp Asn Tyr Gly Thr
                 105                 110

ATCTAGGCCT ATGAAGATCT                                                474
```

(2) INFORMATION FOR SEQ ID NO: 3:

(i) SEQUENCE CHARACTERISTICS:
        (A) LENGTH: 110 amino acids
        (B) TYPE: amino acid
        (D) TOPOLOGY: linear (i i) MOLECULE TYPE: protein (x i) SEQUENCE DESCRIPTION: SEQ ID NO: 3:

```
Met Asp Ala Met Lys Arg Gly Leu Cys Cys Val Leu Leu Leu Cys Gly
 1               5                  10                  15

Ala Val Phe Val Ser Pro Ser Gln Glu Ile His Ala Arg Phe Arg Arg
             20                  25                  30

Gly Ala Arg Ser Thr Leu Gln Gln Glu Lys Pro Asp Phe Cys Phe Leu
         35                  40                  45

Glu Glu Asp Pro Gly Ile Cys Arg Gly Tyr Ile Thr Arg Tyr Phe Tyr
     50                  55                  60

Asn Asn Gln Thr Lys Gln Cys Glu Arg Phe Lys Tyr Gly Gly Cys Leu
 65                  70                  75                  80

Gly Asn Met Asn Asn Phe Glu Thr Leu Glu Glu Cys Lys Asn Ile Cys
                 85                  90                  95

Glu Asp Gly Pro Asn Gly Phe Gln Val Asp Asn Tyr Gly Thr
            100                 105                 110
```

(2) INFORMATION FOR SEQ ID NO: 4:

(i) SEQUENCE CHARACTERISTICS:
  (A) LENGTH: 693 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 105..656

(xi) SEQUENCE DESCRIPTION: SEQ ID NO: 4:

```
GTCGACAGAG CTGAGATCCT ACAGGAGTCC AGGGCTGGAG AGAAAACCTC TGCGAGGAAA        60

GGGAAGGAGC AAGCCGTGAA TTTAAGGGAC GCTGTGAAGC AATC ATG GAT GCA ATG       116
                                                 Met Asp Ala Met
                                                  1

AAG AGA GGG CTC TGC TGT GTG CTG CTG CTG TGT GGA GCA GTC TTC GTT        164
Lys Arg Gly Leu Cys Cys Val Leu Leu Leu Cys Gly Ala Val Phe Val
 5              10                  15                      20

TCG CCC AGC CAG GAA ATC CAT GCC CGA TTC AGA AGA GGA GCC AGA TCA        212
Ser Pro Ser Gln Glu Ile His Ala Arg Phe Arg Arg Gly Ala Arg Ser
             25              30                  35

GAG CTC CCA CCA CTG AAA CTT ATG CAT TCA TTT TGT GCA TTC AAG GCG        260
Glu Leu Pro Pro Leu Lys Leu Met His Ser Phe Cys Ala Phe Lys Ala
         40              45                  50

GAT GAT GGG CCC TGT AAA GCA ATC ATG AAA AGA TTT TTC TTC AAT ATT        308
Asp Asp Gly Pro Cys Lys Ala Ile Met Lys Arg Phe Phe Phe Asn Ile
     55              60                  65

TTC ACT CGA CAG TGC GAA GAA TTT ATA TAT GGG GGA TGT GAA GGA AAT        356
Phe Thr Arg Gln Cys Glu Glu Phe Ile Tyr Gly Gly Cys Glu Gly Asn
 70              75                  80

CAG AAT CGA TTT GAA AGT CTG GAA GAG TGC AAA AAA ATG TGT ACA AGA        404
Gln Asn Arg Phe Glu Ser Leu Glu Glu Cys Lys Lys Met Cys Thr Arg
 85              90                  95                     100

GAT AAT GCA AAC AGG ATT ATA AAG ACA ACA CTG CAG CAA GAA AAG CCA        452
Asp Asn Ala Asn Arg Ile Ile Lys Thr Thr Leu Gln Gln Glu Lys Pro
             105             110                 115

GAT TTC TGC TTT TTG GAA GAG GAT CCT GGA ATA TGT CGA GGT TAT ATT        500
Asp Phe Cys Phe Leu Glu Glu Asp Pro Gly Ile Cys Arg Gly Tyr Ile
         120             125                 130

ACC AGG TAT TTT TAT AAC AAT CAG ACA AAA CAG TGT GAA AGG TTC AAG        548
Thr Arg Tyr Phe Tyr Asn Asn Gln Thr Lys Gln Cys Glu Arg Phe Lys
     135             140                 145

TAT GGT GGA TGC CTG GGC AAT ATG AAC AAT TTT GAG ACA CTC GAG GAA        596
Tyr Gly Gly Cys Leu Gly Asn Met Asn Asn Phe Glu Thr Leu Glu Glu
 150             155                 160

TGC AAG AAC ATT TGT GAA GAT GGT CCG AAT GGT TTC CAG GTG GAT AAT        644
Cys Lys Asn Ile Cys Glu Asp Gly Pro Asn Gly Phe Gln Val Asp Asn
165             170                 175                 180

TAT GGT ACC TGAAGATCTG AATTCTGAAG ATCTAGGCCT ATGAAGATCT                693
Tyr Gly Thr
```

(2) INFORMATION FOR SEQ ID NO: 5:

(i) SEQUENCE CHARACTERISTICS:
  (A) LENGTH: 183 amino acids
  (B) TYPE: amino acid
  (D) TOPOLOGY: linear (ii) MOLECULE TYPE: protein (xi) SEQUENCE DESCRIPTION: SEQ ID NO: 5:

```
Met Asp Ala Met Lys Arg Gly Leu Cys Cys Val Leu Leu Leu Cys Gly
 1               5                  10                  15
```

```
Ala Val Phe Val Ser Pro Ser Gln Glu Ile His Ala Arg Phe Arg Arg
         20                  25                  30

Gly Ala Arg Ser Glu Leu Pro Pro Leu Lys Leu Met His Ser Phe Cys
         35                  40                  45

Ala Phe Lys Ala Asp Asp Gly Pro Cys Lys Ala Ile Met Lys Arg Phe
         50                  55                  60

Phe Phe Asn Ile Phe Thr Arg Gln Cys Glu Glu Phe Ile Tyr Gly Gly
 65                  70                  75                  80

Cys Glu Gly Asn Gln Asn Arg Phe Glu Ser Leu Glu Glu Cys Lys Lys
                 85                  90                  95

Met Cys Thr Arg Asp Asn Ala Asn Arg Ile Ile Lys Thr Thr Leu Gln
            100                 105                 110

Gln Glu Lys Pro Asp Phe Cys Phe Leu Glu Glu Asp Pro Gly Ile Cys
            115                 120                 125

Arg Gly Tyr Ile Thr Arg Tyr Phe Tyr Asn Asn Gln Thr Lys Gln Cys
    130                 135                 140

Glu Arg Phe Lys Tyr Gly Gly Cys Leu Gly Asn Met Asn Asn Phe Glu
145                 150                 155                 160

Thr Leu Glu Glu Cys Lys Asn Ile Cys Glu Asp Gly Pro Asn Gly Phe
                165                 170                 175

Gln Val Asp Asn Tyr Gly Thr
                180
```

( 2 ) INFORMATION FOR SEQ ID NO: 6:

( i ) SEQUENCE CHARACTERISTICS:
        ( A ) LENGTH: 614 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 8..577

( x i ) SEQUENCE DESCRIPTION: SEQ ID NO: 6:

```
GTCGACC ATG ATT TAC ACA ATG AAG AAA GTA CAT GCA CTT TGG GCT AGC         49
        Met Ile Tyr Thr Met Lys Lys Val His Ala Leu Trp Ala Ser
         1               5                  10

GTA TGC CTG CTG CTT AAT CTT GCC CCT GCC CCT CTT AAT CGT GAT TCT         97
Val Cys Leu Leu Leu Asn Leu Ala Pro Ala Pro Leu Asn Arg Asp Ser
 15                  20                  25                  30

GAG GAA GAT GAA GAA CAC ACA ATT ATC ACA GAT ACG GAG CTC CCA CCA        145
Glu Glu Asp Glu Glu His Thr Ile Ile Thr Asp Thr Glu Leu Pro Pro
                 35                  40                  45

CTG AAA CTT ATG CAT TCA TTT TGT GCA TTC AAG GCG GAT GAT GGG CCC        193
Leu Lys Leu Met His Ser Phe Cys Ala Phe Lys Ala Asp Asp Gly Pro
            50                  55                  60

TGT AAA GCA ATC ATG AAA AGA TTT TTC TTC AAT ATT TTC ACT CGA CAG        241
Cys Lys Ala Ile Met Lys Arg Phe Phe Phe Asn Ile Phe Thr Arg Gln
    65                  70                  75

TGC GAA GAA TTT ATA TAT GGG GGA TGT GAA GGA AAT CAG AAT CGA TTT        289
Cys Glu Glu Phe Ile Tyr Gly Gly Cys Glu Gly Asn Gln Asn Arg Phe
80                  85                  90

GAA AGT CTG GAA GAG TGC AAA AAA ATG TGT ACA AGA GAT AAT GCA AAC        337
Glu Ser Leu Glu Glu Cys Lys Lys Met Cys Thr Arg Asp Asn Ala Asn
 95                 100                 105                 110

AGG ATT ATA AAG ACA ACA CTG CAG CAA GAA AAG CCA GAT TTC TGC TTT        385
Arg Ile Ile Lys Thr Thr Leu Gln Gln Glu Lys Pro Asp Phe Cys Phe
```

-continued

```
                         115                          120                           125
TTG  GAA  GAG  GAT  CCT  GGA  ATA  TGT  CGA  GGT  TAT  ATT  ACC  AGG  TAT  TTT        433
Leu  Glu  Glu  Asp  Pro  Gly  Ile  Cys  Arg  Gly  Tyr  Ile  Thr  Arg  Tyr  Phe
               130                      135                           140

TAT  AAC  AAT  CAG  ACA  AAA  CAG  TGT  GAA  AGG  TTC  AAG  TAT  GGT  GGA  TGC        481
Tyr  Asn  Asn  Gln  Thr  Lys  Gln  Cys  Glu  Arg  Phe  Lys  Tyr  Gly  Gly  Cys
          145                      150                           155

CTG  GGC  AAT  ATG  AAC  AAT  TTT  GAG  AGA  CTC  GAG  GAA  TGC  AAG  AAC  ATT        529
Leu  Gly  Asn  Met  Asn  Asn  Phe  Glu  Arg  Leu  Glu  Glu  Cys  Lys  Asn  Ile
     160                           165                      170

TGT  GAA  GAT  GGT  CCG  AAT  GGT  TTC  CAG  GTG  GAT  AAT  TAT  GGT  ACC  TGAAGATCT  584
Cys  Glu  Asp  Gly  Pro  Asn  Gly  Phe  Gln  Val  Asp  Asn  Tyr  Gly  Thr
175                     180                           185                 190

AATTCTGAAG ATCTAGGCCT ATGAAGATCT                                                       614
```

( 2 ) INFORMATION FOR SEQ ID NO: 7:

( i ) SEQUENCE CHARACTERISTICS:
        ( A ) LENGTH: 189 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 7:

```
Met  Ile  Tyr  Thr  Met  Lys  Lys  Val  His  Ala  Leu  Trp  Ala  Ser  Val  Cys
 1                    5                    10                        15

Leu  Leu  Leu  Asn  Leu  Ala  Pro  Ala  Pro  Leu  Asn  Arg  Asp  Ser  Glu  Glu
               20                   25                        30

Asp  Glu  Glu  His  Thr  Ile  Ile  Thr  Asp  Thr  Glu  Leu  Pro  Pro  Leu  Lys
          35                   40                        45

Leu  Met  His  Ser  Phe  Cys  Ala  Phe  Lys  Ala  Asp  Asp  Gly  Pro  Cys  Lys
     50                   55                        60

Ala  Ile  Met  Lys  Arg  Phe  Phe  Phe  Asn  Ile  Phe  Thr  Arg  Gln  Cys  Glu
65                   70                        75                            80

Glu  Phe  Ile  Tyr  Gly  Gly  Cys  Glu  Gly  Asn  Gln  Asn  Arg  Phe  Glu  Ser
               85                        90                            95

Leu  Glu  Glu  Cys  Lys  Lys  Met  Cys  Thr  Arg  Asp  Asn  Ala  Asn  Arg  Ile
               100                       105                 110

Ile  Lys  Thr  Thr  Leu  Gln  Gln  Glu  Lys  Pro  Asp  Phe  Cys  Phe  Leu  Glu
          115                       120                 125

Glu  Asp  Pro  Gly  Ile  Cys  Arg  Gly  Tyr  Ile  Thr  Arg  Tyr  Phe  Tyr  Asn
     130                       135                 140

Asn  Gln  Thr  Lys  Gln  Cys  Glu  Arg  Phe  Lys  Tyr  Gly  Gly  Cys  Leu  Gly
145                       150                 155                            160

Asn  Met  Asn  Asn  Phe  Glu  Arg  Leu  Glu  Glu  Cys  Lys  Asn  Ile  Cys  Glu
               165                       170                       175

Asp  Gly  Pro  Asn  Gly  Phe  Gln  Val  Asp  Asn  Tyr  Gly  Thr
               180                       185
```

ANTICOAGULANT ANALOGUES OF THE TISSUE FACTOR EXTRINSIC PATHWAY INHIBITOR (EPI) WITH REDUCED AFFINITY FOR HEPARIN

FIELD OF THE INVENTION

The present invention relates to new protein analogues of the Extrinsic Pathway Inhibitor (EPI; also known as Tissue Factor Pathway Inhibitor, TFPI, or Lipoprotein-Associated Pathway Inhibitor, LACI). The invention also features a method of making the analogues and therapeutic preparations containing them.

BACKGROUND OF THE INVENTION

Blood coagulation is a complex process involving many activating and inactivating coagulation factors. Anticoagulant proteins are known to be important for regulation of the coagulation process (see B. Lämmle and J. Griffin (Clinics in Haematology 14 (1985), 281-342) and anticoagulants are thus important in the treatment of a variety of diseases, e.g. thrombosis, myocardial infarction, disseminated intravascular coagulation etc.

Thus heparin is used clinically to increase the activity of antithrombin III and heparin cofactor II. Antithrombin III is used for the inhibition of factor Xa and thrombin. Hirudin is used for the inhibition of thrombin and protein C may be used for the inhibition of factor V and factor VIII.

Anticoagulant proteins may also be used in the treatment of cancer. Thus, antistatin has been shown to have anti-metastatic properties (J. H. Han et al., Gene 75 (1989), 47-57). Also heparin and warfarin have been shown to possess antimetastatic properties (G. J. Gasic et al., Int. Rev. Exp. Pathol. 29 (1985), 173-209).

Coagulation can be initiated through the extrinsic pathway by the exposure of tissue factor (TF) to the circulating blood (Y. Nemerson, Blood 71 (1988), 1-8). Tissue factor is a protein cofactor for factor VII/VIIa and binding of tissue factor enhances the enzymatic activity of factor VIIa (FVIIa) towards its substrates factor IX and factor X. Placenta anticoagulant protein is able to inhibit tissue factor activity, probably by interfering with TF/FVIIa-phospholipid interaction (S. Kondo et al., Thromb. Res. 48 (1987), 449-459).

Recently a new anticoagulant protein, the extrinsic pathway inhibitor (EPI) has been isolated (Broze et al., Proc. Natl. Acad. Sci. 84 (1987), 1886-1890).

On a molar basis EPI has been shown to be a potent inhibitor of TF/FVIIa induced coagulation (R. A. Gramzinski et al., Blood 73 (1989), 983-989). EPI binds and inhibits factor Xa (FXa) and the complex between EPI and FXa inhibits TF/FVIIa (Rapaport, Blood 73 (1989), 359-365). EPI is especially interesting as an anticoagulant/antimetastatic agent as many tumor cells express TF activity (T. Sakai et al., J. Biol. Chem. 264 (1989), 9980-9988) and because EPI shows anti-Xa activity like antistatin.

EPI has been recovered by Broze et al. (supra) from HepG2 hepatoma cells (Broze EP A 300988) and the gene for the protein has been cloned (Broze EP A 318451). A schematic diagram over the secondary structure of EPI is shown in FIG. 1 and the amino acid sequence of EPI is shown in FIG. 2 where the N-terminal amino acid Asp is given the number 1. The protein consists of 276 amino acid residues and has in addition to three inhibitor domains of the Kunitz type three potential glycosylation sites at position Asn117, Asn167 and Asn229. The molecular weight shows that some of these sites are glycosylated. Furthermore, it has been shown that the second Kunitz domain binds FXa while the first Kunitz domain binds FVIIa/TF (Girard et al., Nature 338 (1989), 518-520). EPI has also been isolated from HeLa cells (PCT/DK90/00016) and it was shown that HeLa EPI binds heparin.

Heparin binding is an important factor for the pharmacokinetics of substances for injection. It has been shown that platelet factor 4 (M. Prosdomi et al., Thromb. Res. 39 (1985), 541-547) and aprotinin with one Kunitz domain (Arzneimittelforschung, 33 (4) 479-94, 1983) has a short half life probably due to the heparin binding properties. Lowering of the heparin binding capacity of an anticoagulant would therefore seem to be advantageous. Furthermore, it might be advantageous to use a smaller molecule than EPI for the medical treatment.

It has according to the present invention surprisingly been found that certain EPI analogues retain the EPI activity as well as anti Xa activity although parts of the molecule has been deleted. Furthermore, these analogues show a much lower affinity for heparin than full length EPI, making them more useful as therapeutic agents than the native molecule. The EPI analogues will furthermore have a longer half life as compared with native EPI which will further reduce the amount of active ingredients for the medical treatment.

SUMMARY OF THE INVENTION

In its first aspect the present invention is related to novel EPI analogues wherein one or more of the amino acid residues of native EPI have been deleted.

In its second aspect the present invention is related to a new group of EPI analogues having EPI activity but with no or low heparin binding capacity under physiological conditions (pH, ionic strength).

In the present context the term "low heparin binding capacity" is intended to mean a binding capacity of about 50%, more preferably of about 25% and most prefereably less than about 10% of that of native EPI at physiological pH and ionic strength.

The preferred group of the novel EPI analogues can be characterized as being devoid of the heparin binding domain cf native EPI or having a non-functional heparin binding domain by having deleted one or more of the amino acid residues in said domain resulting in loss or a substantial lowering of the heparin binding capacity. The same effect may also be obtained by substituting one or more of the amino acid residues in the heparin binding domain with another amino acid residue.

DETAILED DESCRIPTION OF THE INVENTION

To retain the EPI activity the analogues according to the present invention should at least contain the N-terminal sequence including the first and second Kunitz domain. Thus, the EPI analogues according to the present invention should at least contain the amino acid sequence from amino acid number 25 to amino acid number 148 of native EPI (see FIG. 1 and 2).

It has been shown by the inventors hereof that the heparin binding capacity is lost when the sequence from amino acid residue number 162 to amino acid residue number 275 is deleted from the EPI molecule. It is therefore concluded that the heparin binding domain is situated in this part of the EPI molecule. It is assumed that the heparin binding domain comprises at least a region from Arg246 to Lys265 near the C-terminal end of the EPI molecule being rich in positively charged amino acid residues.

Preferred EPI analogues according to the present invention are such in which one or more amino acid residues have been deleted in the native EPI molecule from amino acid residue Glu148 to the C-terminal Met276.

More specifically, one or more amino acid residues in the sequence from Arg246 to Lys275 have been deleted.

Examples of EPI analogues according to the present invention are:

(Asp1 - Thr255)-EPI
(Asp1 - Ile253)-EPI
(Asp1 - Lys249)-EPI
(Asp1 - Ser248)-EPI
(Asp1 - Lys240)-EPI
(Asp1 - Glu234)-EPI
(Asp1 - Trp188)-EPI
(Asp1 - Asn164)-EPI
(Asp1 - Thr161)-EPI
(Asp1 - Asp149)-EPI
(Asp1 - Glu148)-EPI
Ser-(Asp1 - Thr255)-EPI
Ser-(Asp1 - Ile253)-EPI
Ser-(Asp1 - Lys249)-EPI
Ser-(Asp1 - Ser248)-EPI
Ser-(Asp1 - Lys240)-EPI
Ser-(Asp1 - Glu234)-EPI
Ser-(Asp1 - Trp188)-EPI
Ser-(Asp1 - Asn164)-EPI
Ser-(Asp1 - Thr161)-EPI
Ser-(Asp1 - Asp149)-EPI
Ser-(Asp1 - Glu148)-EPI
(Glu15 - Thr255)-EPI
(Glu15 - Ile253)-EPI
(Glu15 - Lys249)-EPI
(Glu15 - Ser248)-EPI
(Glu15 - Lys240)-EPI
(Glu15 - Glu234)-EPI
(Glu15 - Trp188)-EPI
(Glu15 - Asn164)-EPI
(Glu15 - Thr161)-EPI
(Glu15 - Asp149)-EPI
(Glu15 - Glu148)-EPI
Ser-(Glu15 - Thr255)-EPI
Ser-(Glu15 - Ile253)-EPI
Ser-(Glu15 - Lys249)-EPI
Ser-(Glu15 - Ser248)-EPI
Ser-(Glu15 - Lys240)-EPI
Ser-(Glu15 - Glu234)-EPI
Ser-(Glu15 - Trp188)-EPI
Ser-(Glu15 - Asn164)-EPI
Ser-(Glu15 - Thr161)-EPI
Ser-(Glu15 - Asp149)-EPI
Ser-(Glu15 - Glu148)-EPI
(Ser24 - Thr255)-EPI
(Ser24 - Ile253)-EPI
(Ser24 - Lys249)-EPI
(Ser24 - Ser248)-EPI
(Ser24 - Lys240)-EPI
(Ser24 - Glu234)-EPI
(Ser24 - Trp188)-EPI
(Ser24 - Asn164)-EPI
(Ser24 - Thr161)-EPI
(Ser24 - Asp149)-EPI
(Ser24 - Glu148)-EPI
(Asp1 - Thr255)-(Ile266 - Met276)-EPI
(Asp1 - Ile253)-(Ile266 - Met276)-EPI
(Asp1 - Ser248)-(Ile266 - Met276)-EPI
(Asp1 - Gln245)-(Ile266 - Met276)-EPI
(Asp1 - Thr255)-(Val264 - Met276)-EPI
(Asp1 - Ile253)-(Val264 - Met276)-EPI
(Asp1 - Ser248)-(Val264 - Met276)-EPI
(Asp1 - Glu245)-(Val264 - Met276)-EPI
(Asp1 - Thr255)-(Glu262 - Met276)-EPI
(Asp1 - Ile253)-(Glu262 - Met276)-EPI

-continued (Asp1 - Ser248)-(Glu262 - Met276)-EPI
(Asp1 - Glu245)-(Glu262 - Met276)-EPI
Ser-(Asp1 - Thr255)-(Ile266 - Met276)-EPI
Ser-(Asp1 - Ile253)-(Ile266 - Met276)-EPI
Ser-(Asp1 - Ser248)-(Ile266 - Met276)-EPI
Ser-(Asp1 - Gln245)-(Ile266 - Met276)-EPI
Ser-(Asp1 - Thr255)-(Val264 - Met276)-EPI
Ser-(Asp1 - Ile253)-(Val264 - Met276)-EPI
Ser-(Asp1 - Ser248)-(Val264 - Met276)-EPI
Ser-(Asp1 - Glu245)-(Val264 - Met276)-EPI
Ser-(Asp1 - Thr255)-(Glu262 - Met276)-EPI
Ser-(Asp1 - Ile253)-(Glu262 - Met276)-EPI
Ser-(Asp1 - Ser248)-(Glu262 - Met276)-EPI
Ser-(Asp1 - Glu245)-(Glu262 - Met276)-EPI In addition to the described deletions in the EPI molecule, certain amino acid residues of native EPI may also be replaced by another naturally occurring amino acid residue. The EPI analogues may also advantageously contain a Ser residue as the N-terminal residue. This is necessary if a signal sequence is used requiring an N-terminal Ser in the mature protein as a recognition site for cleavage. Thus, the N-terminal in the EPI molecule may be replaced by a Ser or an additional Ser may be inserted adjacent to the original N-terminal residue. Also the potential glycosylation sites at Asn167 and Asn238 may be substituted by another amino acid residue to avoid glycosylation.

It has not previously been shown that glycosylation sites are dispensable for EPI activity. Neither has it been shown that large fragments of the EPI protein are dispensable for EPI activity, i.e. for FXa dependent inhibition of TF/FVIIa. It has previously been shown that a single amino acid in EPI can be replaced by another amino acid residue (Arg199—>Leu199), (Girard et al., Nature 338 (1989), 518–520) without affecting the activity. However, such a change does not significantly change the structure of the protein. In contrast hereto the deletions according to the present invention give rise to new molecules with other properties than the native molecule, as illustrated by the changed affinity for heparin.

The present EPI-analogues may be produced by well-known recombinant DNA technology.

The gene for the native EPI has been cloned and sequenced (Wun et al., J. Biol. Chem. 263 (1988), 6001–6004). DNA-sequences encoding the desired EPI-analogue may be contructed by altering EPI cDNA by site-directed mutagenesis using synthetic oligonucleotides encoding the desired amino acid sequence for homologous recombination in accordance with well-known procedures.

The DNA sequence encoding the EPI analogue of the invention may also be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

In a further aspect, the present invention relates to a recombinant expression vector which comprises a DNA sequence encoding the EPI analogue of the invention. The expression vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the EPI analogue of the invention should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding the EPI analogue of the invention in mammalian cells are the SV 40 promoter (Subramani et al., *Mol.Cell Biol.* 1, 1981, pp. 854–864), the MT-1 (metallothionein gene) promoter (Palmiter et al., *Science* 222, 1983, pp. 809–814), the adenovirus 2 major late promoter or the CMV (cytomegalovirus IE1) promoter (Henninghausen et al., *EMBO J.* 5 (1986), 1367-71) Suitable promoters for use in yeast host cells include promoters from yeast glycolytic genes (Hitzeman et al., *J.Biol.Chem.* 255, 1980, pp. 12073–12080; Alber and Kawasaki, *J.Mol.Appl.Gen.* 1, 1982, pp. 419–434) or alcohol dehydrogenase genes (Young et al., in *Genetic Engineering of Microorganisms for Chemicals* (Hollaender et al., eds.), Plenum Press, New York, 1982), or the PTI1 (U.S. Pat. No. 4,599,311) or ADH2-4c (Russell et al., *Nature* 304, 1983, pp. 652–654) promoters. Suitable promoters for use in filamentous fungus host cells are, for instance, the ADH3 promoter (McKnight et al., *The EMBO J.* 4, 1985, pp. 2093-2099) or the tipA promoter.

To ensure secretion a suitable signal sequence is inserted at the 5' of the DNA sequence encoding the EPI analogue. A suitable signal sequence is the t-PA signal sequence (Friezner et al., J.Biol.Chem. 261 (1986), 6972-85).

The DNA sequence encoding the EPI analogue of the invention should also be operably connected to a suitable terminator, such as the human growth hormone terminator (Palmiter et al., op. cit.) or (for fungal hosts) the TPII (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector of the invention may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate.

The procedures used to ligate the DNA sequences coding for the EPI analogue of the invention, the promoter and the terminator, respectively, and to insert them into suitable vectors containing the information necessary for replication, are well known to persons skilled in the art (cf., for instance, Sambrook et al., op. cit.).

In a further aspect, the present invention relates to a cell which contains the recombinant expression vector described above. The host cell may be any cell which is capable of producing the EPI analogue and is preferably a eukaryotic cell, in particular a mammalian cell. Examples of suitable mammalian cell lines are the COS (ATCC CRL 1650 and 1651), BHK (ATCC CRL 1632, ATCC CCL 10) or CHO (ATCC CCL 61) cell lines. Methods of transfecting mammalian cells and expressing DNA sequences introduced in the cells are described in e.g. Kaufman and Sharp, *J.Mol.Biol.* 159, 1982, pp. 601–621; Southern and Berg, *J.Mol.Appl.Genet.* 1, 1982, pp. 327–341; Loyter et al., *Proc.Natl.Acad.Sci. USA* 79, 1982, pp. 422–426; Wigler et al., *Cell* 14, 1978, p. 725; Corsaro and Pearson, *Somatic Cell Genetics* 7, 1981, p. 603, Graham and van der Eb, *Virology* 52, 1973, p. 456; and Neuman et al., *EMBO J.* 1, 1982, pp. 841–845.

Alternatively, fungal cells (including yeast cells) may be used as host cells of the invention. Examples of suitable yeast cells include cells of Saccharomyces spp. or Schizosaccharomyces spp., in particular strains of *Saccharomyces cerevisiae*. Examples of other fungal cells are cells of filamentous fungi, e.g. Aspergillus spp. or Neurospora spp., in particular strains of *Aspergillus oryzae* or *Aspergillus niger*. The use of Aspergillus spp. for the expression of proteins is described in, e.g., EP 272,277.

In a still further aspect the present invention relates to a process for producing an EPI analogue according to the invention, which comprises culturing a cell as described above in a suitable nutrient medium under conditions which are conductive to the expression of the EPI analogue, and recovering the polypeptide from the culture. The medium used to culture the cells may be any conventional medium suitable for growing mammalian cells, such as a serum-containing or serum-free medium containing appropriate supplements. Suitable media are available from commercial suppliers or may be prepared according to published recipes (e.g. in catalogues of the American Type Culture Collection).

The EPI analogue will preferably be secreted to the growth medium and may be recovered from the medium by conventional procedures including separating the host cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

The novel EPI analogues may be used for the treatment of patients having coagulation disorders or cancer.

Accordingly the invention is also related to a pharmaceutical preparation for the treatment of patients having coagulation disorders or cancer containing an EPI analogue in a suitable amount together with suitable adjuvants and additions.

The pharmaceutical preparations may be in a buffered aqueous solution with appropriate stabilizers and preservatives. The solution may be heat treated and may be contained in ampoules or in carpoules for injection pens. Alternatively the stabilized solution may be freeze dried and contained in ampoules or in two chamber injection systems with freeze dried substance in one chamber and solvent in the other chamber.

BRIEF DESCRIPTION OF THE DRAWINGS

The present invention is further described with reference to the drawings in which FIG. 2 shows the amino acid sequence of native EPI (SEQ ID NO: 1), FIG. 7 shows the DNA and amin acid sequence for Ser-(Thr88-Thr161)-EPI preceded by the t-PA signal sequence (SEQ ID NOs: 2 and 3), FIGS. 8A and 8B together show the DNA, and amino acid sequence for the Ser-(Glu15 - Thr161)-EPI preceded by the t-PA signal sequence (SEQ ID NOs: 4 and 5)

Figure 1:
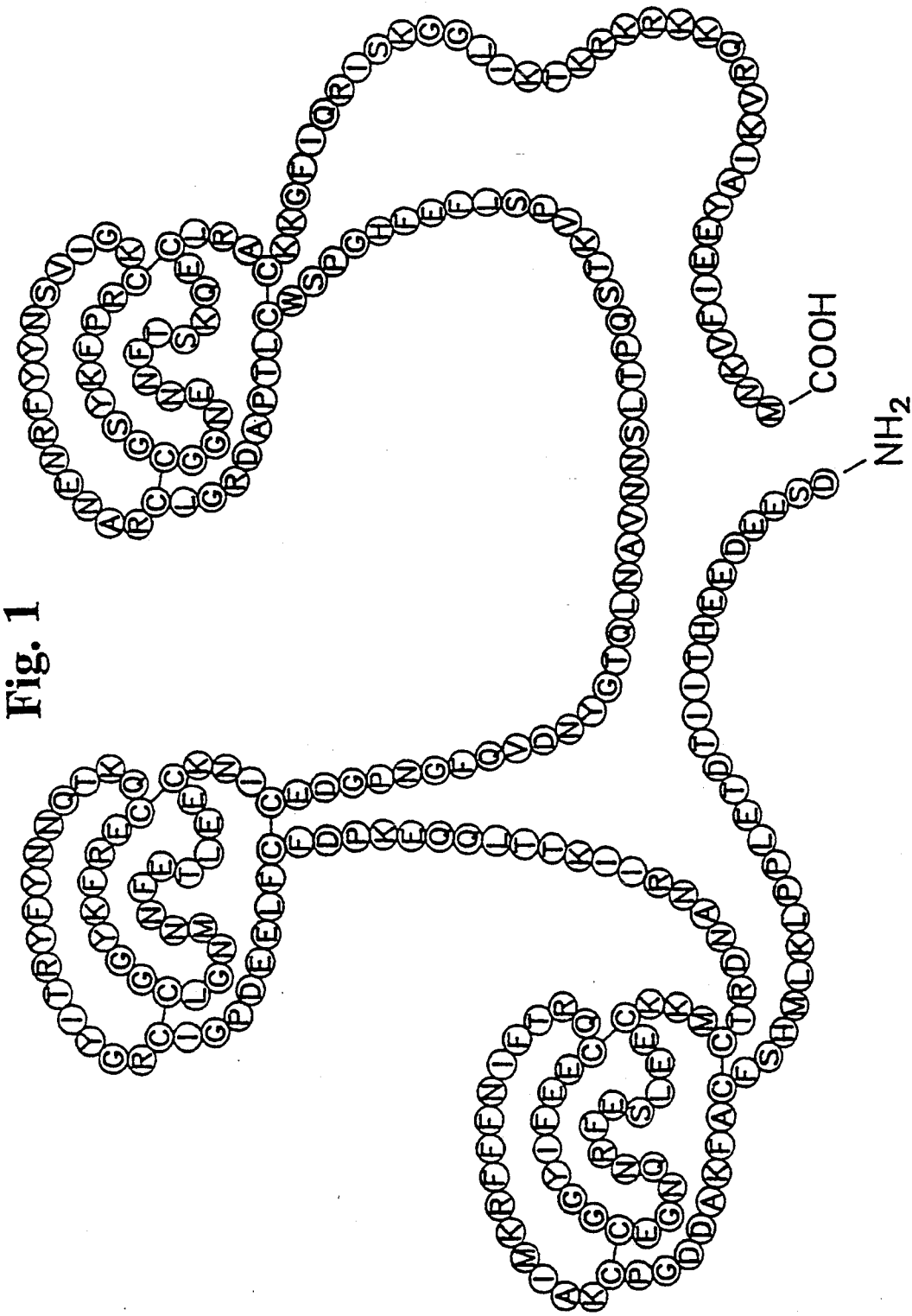
FIG. 1 shows the amino acid sequence and the two dimensional structure of EPI.

The invention is further described in the following examples which are not in any ways intended to limit the scope or spirit of the invention as claimed.

Experimental Part

Assay for EPI activity: EPI was measured in a chromogenic microplate assay, modified after the method of Sandset et al., (Thromb. Res. 47 (1989), 389–400). Heat treated plasma pool was used as a standard. This standard is set to contain 1 U/ml of EPI activity. Standards and samples were diluted in buffer A (0.05M tris/0.1M NaCl/0.1M Na-citrate/0.02% NaN$_3$/pH 8.0) containing 2 µg/ml polybrene and 0.2% bovine serum albumin. FVIIa/TF/FX/CaCl$_2$ combination reagent was prepared in buffer A and contained 1.6 ng/ml FVIIa (Novo-Nordisk a/s), human tissue factor diluted 60 fold (Hjort, Scand. J. Clin. Lab. Invest. 9 (1957), 50 ng/ml FX (Sigma) and 18 mM CaCl$_2$. The assay was performed in microplate strips at 37° C. 50 µl of samples and standards were pipetted into the strips and 100 µl combination reagent was added to each well. After 10 minutes incubation, 25 µl of FX (3.2 µg/ml) was added to each well and after another 10 minutes 25 1 of chromogenic substrate for FXa (S2222) was added 10 minutes after the addition of substrate. The reaction was stopped by addition of 50 µl 1.0M citric acid pH 3.0. The microplate was read at 405 nm.

Assay for anti Xa activity: HeLa EPI purified on heparin sepharose (PCTDK90/00016) was used as a standard. This standard was assigned an amount of Xa inhibition units corresponding to the amount of EPI units measured in the EPI assay. Samples and standards were diluted in 50 mM tris/0.2% bovine serum albumin pH 7.3. 100 µl of diluted samples and standard were incubated 30 minutes at 37° C. with 100 µl FXa (Stago, 14 ng/ml). 25 µl of S2222 (2 mg/ml) was added after another 2 hours at 37° C. The assay was stopped and read like the EPI assay.

Synthetic oligonucleotides were synthesized by the phosphoramidite method using an Applied Biosystem DNA synthesizer.

M13 sequencing primers and gamma-[$^{32}$P]-ATP (5000 Ci/mmol, 10 mCi/ml) for labelling of primers were obtained from Amersham.

Restriction endonucleases and T4 DNA-ligase were obtained from New England Biolabs. Modified T7 DNA-polymerase (Sequenase) was obtained from United States Biochemicals. pBS+ (Stratagene) was used as cloning vector for synthetic DNA fragments.

Figure 3:
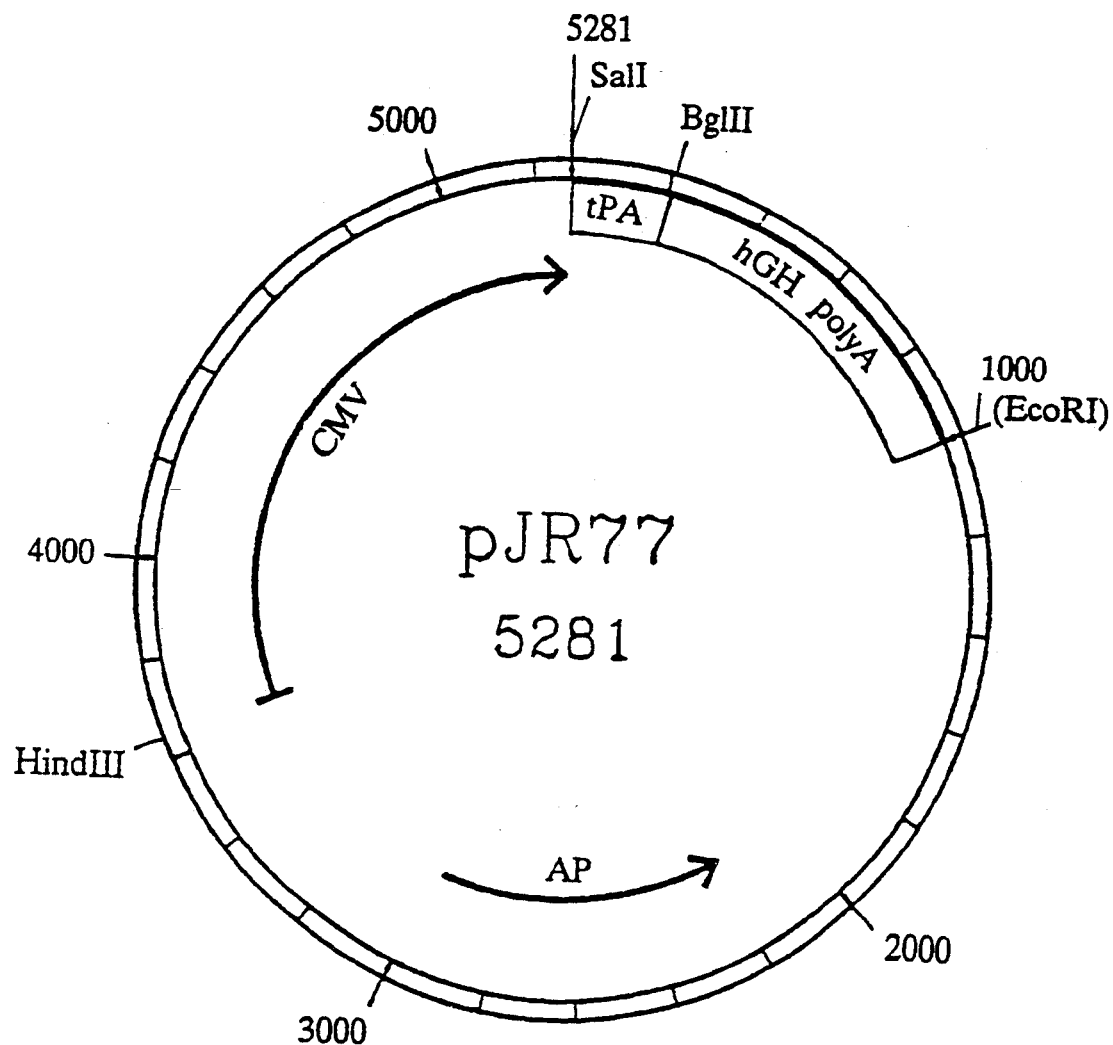
FIG. 3 shows plasmid pJR77 containing the t-PA signal, the human cytomegalovirus IEI gene promoter and the human growth hormone gene polyadenylation signal.
Figure 4:
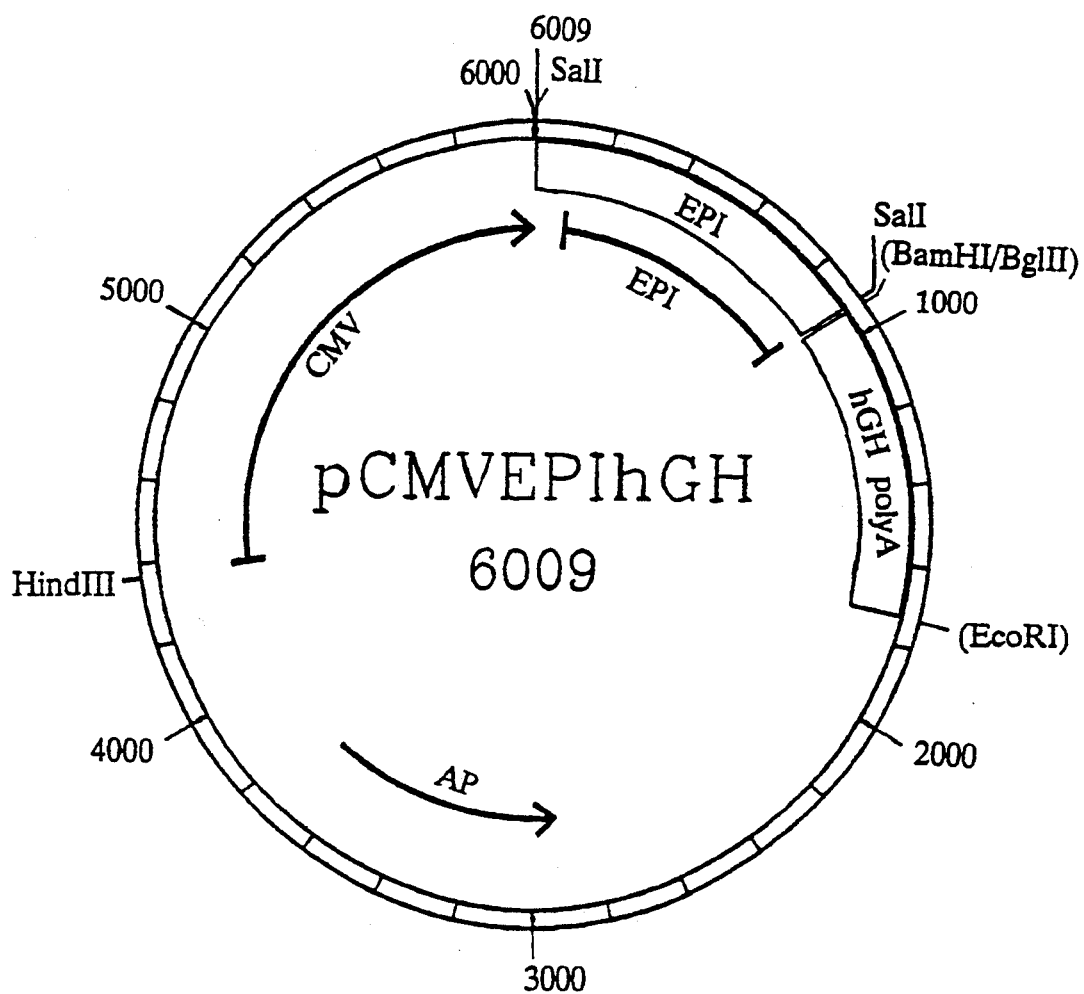
FIG. 4 shows pCMVEPIhGH containing the EPI gene.
Figure 5:
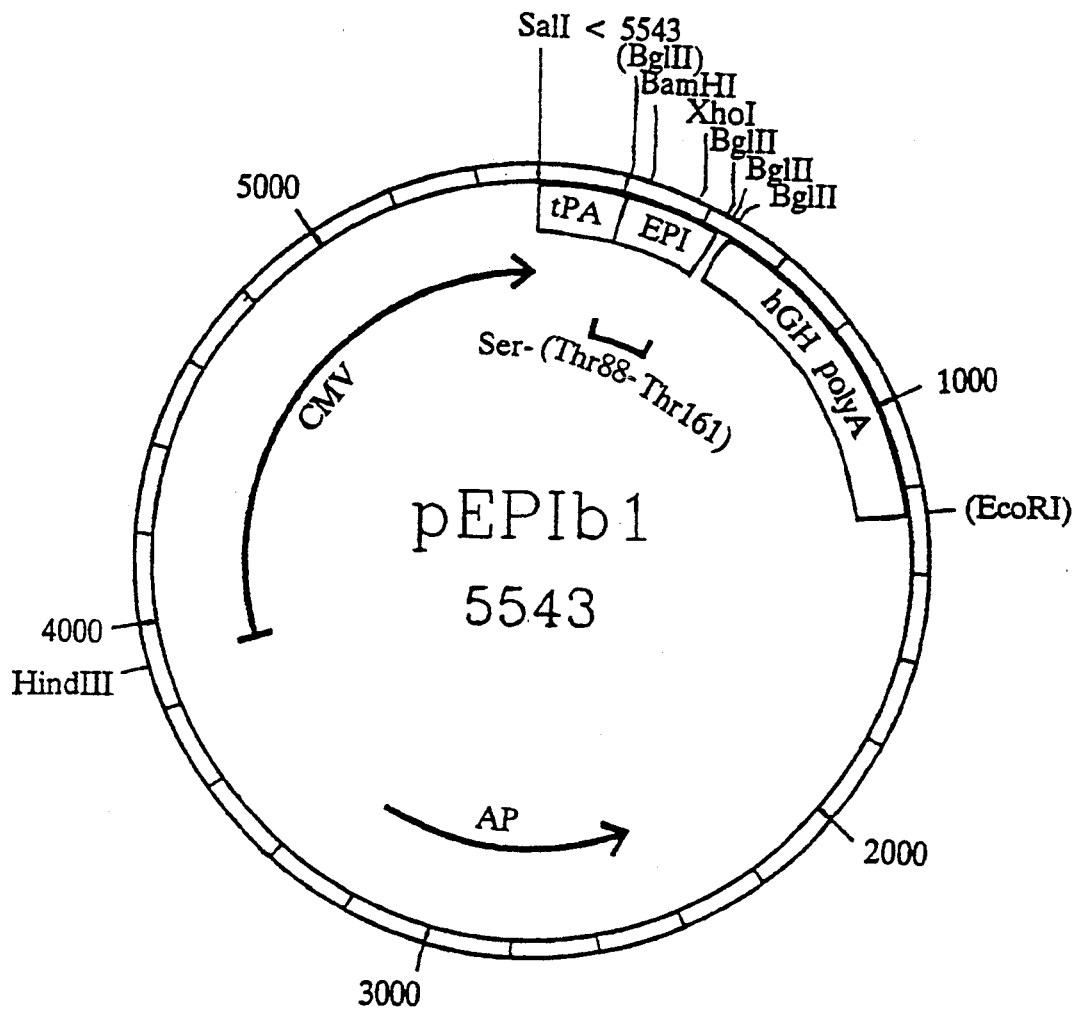
FIG. 5 shows plasmid pEPIb1 containing a DNA sequence encoding Ser-(Thr88- Thr161)-EPI.

A mammalian expression vector denoted pJR77 (FIG. 3) containing the human cytomegalovirus IE1 gene promoter and the human growth hormone gene polyadenylation signal was used for expression of various EPI related proteins in COS-7 cells.

XL-1 Blue (Stratagene) a derivative of *E. coli* K12 as used as bacterial recipient for plasmid transformations and as host for propagation and preparation of plasmid DNA.

Green monkey kidney cell-line COS-7 (ATCC #CRL 1651) was grown in Dulbecco's modified eagle medium (DMEM) (Gibco 041-1965)+50 µg/ml gentamycin+110 µg/ml pyruvate+10% fetal calf serum (FCS) or DMEM+50 µg/ml gentamycin+110 µg/ml pyruvate +1% ITS+ (insulin, transferrin, serum albumin).

Restriction endonucleases and other enzymes were used in accordance with the manufacturers recommendations. Standard recombinant DNA-techniques were carried out as described (Maniatis et al., Molecular cloning. Cold Spring Harbor Laboratory, 1982).

DNA sequences were determined by the dideoxy chain termination method (Sanger et al., Proc. Natl. Acad. Sci. 74 (1977), 5463–67) using double stranded plasmid DNA as template and $^{32}$P-labelled primers and Sequenase.

Plasmid DNA was introduced into COS-7 cells by calcium phosphate coprecipitation (Graham & van der Eb, Virology 52 (1973), 456–457).

$7 \times 10^5$ cells were seeded in 20 cm$^2$ dishes in 5 ml DMEM+FCS. The following day each dish was added 20 µg plasmid DNA in 0.5 precipitate and 50 µl 10 mM chloroquine diphosphate. Cells were incubated overnight with precipitate. The following day fresh medium DMEM+ITS+ was added. After two days of incubation media were harvested and assayed for EPI-activity and anti Xa-activity.

EXAMPLE 1

Preparation of DNA-fragments encoding EPI and EPI analogues and transient expression in COS-7 cells.

The EPI cDNA sequence is described by Wun et al. (J. Biol. Chem. 263 (1988), 6001–6004). Based on the known sequence synthetic DNA-sequences encoding EPI and EPI analogues were constructed by silent mutations introducing restriction endonuclease recognition sites at suitable locations.

Expression cassettes encoding EPI fragments using the tPA signal sequence (FIGS. 7 and 8) and an expression cassette encoding the entire EPI protein were assembled by sequentially insertion into the cloning vector pBS+ of annealed complementary synthetic oligonucleotides. Following assembly of DNA fragment sequences were verified by DNA sequencing as described.

Finally expression casettes were transferred to expression vector pJR77 giving rise to the following expression plasmids:

pEPIb1 encoding the tPA signal followed by EPI analogue Ser-(Thr88-Thr161)-EPI (SEQ ID NO: 2). pEPIab encoding the tPA signal followed by EPI analogue Ser-(Glu15-Thr161)-EPI (SEQ ID NO: 4). pCMVEPIhGH encoding the entire EPI protein.

COS-7 cells were transfected as indicated in Table 1. After 2 days of incubation with DMEM+ITS. media were harvested. Table 1 shows assay results for EPI-activity and anti-Xa activity.

TABLE 1

| Plasmid DNA | EPI [U/ml] | anti-Xa [U/ml] |
| --- | --- | --- |
| pBS+ | 0.19 | 0.19 |
| pCMVEPIhGH | 8.3 | 7.6 |
| pEPIb1 | 0.28 | 0.15 |
| pEPIab | 4.5 | 5.6 |

The results in table 1 show that the EPI-fragment Ser-(Thr88Thr161)-EPI (SEQ ID No. 3) containing only the second Kunitz domain has no activity whereas the EPI-fragment Ser-(Glu15-Thr161)-EPI (SEQ ID NO: 5) containing the first and second Kunitz domain has retained the EPI activity.

EXAMPLE 2

COS transfections with EPI plasmids were performed as described in example 1 and media were harvested after 48 hours. 5 columns were packed, each with 300 ul of heparin sepharose. The columns were equilibrated with 20 mM tris/10% glycerol, pH 7.5. (buffer B). 1.3 ml culture medium was applied to each column. Then the columns were washed with 1.5 ml buffer B and each column was eluted with steps of 1.5 ml buffer B with increasing amounts of NaCl. For comparison is given data from another experiment where EPI from HeLa and HepG2 cells were fractionated on heparin-sepharose. In this experiment other NaCl concentrations were used for elution. Table 2 shows that Ser-(Glu15-Thr161)-EPI (SEQ ID NO: 5) not bind to heparin at physiological pH and ionic strength.

TABLE 2

Heparin binding of EPI and EPI-like proteins

| Culture medium | U EPI in medium | % of EPI activity | | | | | |
| --- | --- | --- | --- | --- | --- | --- | --- |
| | | flow through | B wash | M NaCl | | | |
| | | | | 0.25 | 0.5 | 0.75 | 2.0 |
| untransfected COS | 0.25 | <4 | <4 | <4 | 17 | 54 | 33 |
| EPI-transfected COS | 7.10 | <4 | <4 | <4 | 6 | 48 | <4 |
| Ser-(Glu15-Thr161)-EPI (SEQ ID NO: 6) transfected COS | 8.34 | 76 | 24 | <3 | <3 | <3 | <3 |
| untransfected HeLa | 1.17 | NM | NM | ND | 64 | ND | 15 |
| untransfected HepG2 | 1.95 | NM | NM | ND | 12 | ND | 74 |

NM: not measured, ND: not done

EXAMPLE 3

Preparation of (Asp1-Thr161)-EPI

Construction of expression plasmids, transformation and expression in COS-7 cell was performed using materials and methods as described in Example 1.

Figure 6:
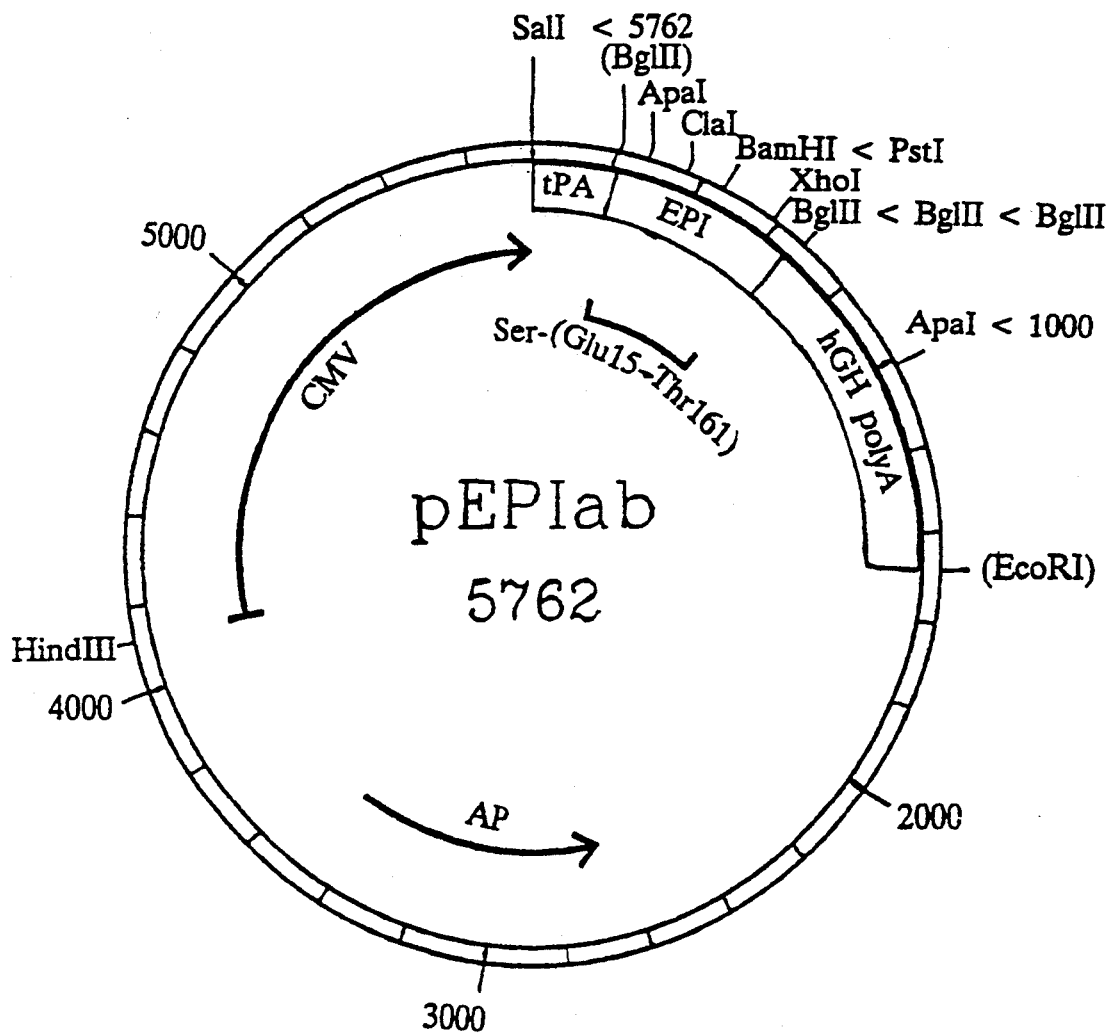
FIG. 6 shows plasmid PEPIab containing a DNA sequence encoding Ser-(Glu15- Thr161)-EPI.

Sequences between SalI and BamHI of expression plasmid pEPIab (FIG. 6) encoding the t-PA signal and Ser-(Glu15-Thr161)-EPI (SEQ ID NO: 5) was replaced by a synthetic DNA-sequence encoding the authentic EPI signal and (Asp1-Thr161)-EPI (SEQ ID NO: 6).

Figure 9:
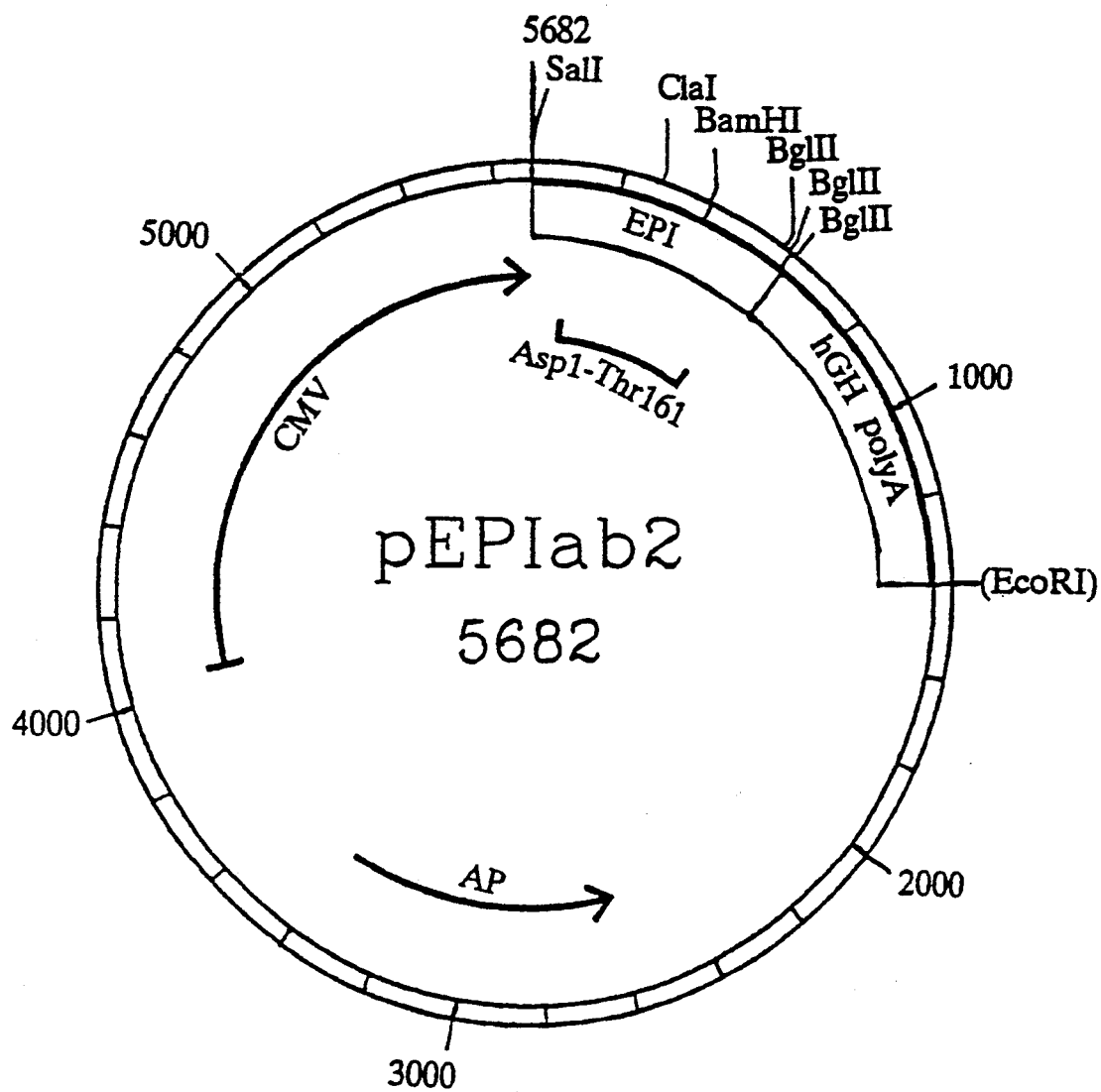
FIG. 9 shows plasmid PEPIab2 containing a DNA sequence encoding (Asp1-Thr161)-EPI, and FIGS. 10A and 10B together show the DNA and amino acid sequence for (Asp1-Thr161)-EPI preceded by the EPI signal (SEQ ID NOs: 6 and 7).

The resulting plasmid pEPIab2 is shown in FIG. 9 and the expression cassette of pEPIab2 is shown in FIG. 10.

Culture medium from pEPIab2 transfected COS cells were applied to Heparin-Sepharose as described in Example 2. 3.8 ml culture medium containing 31.2 U/ml of EPI was applied to a 0.5 ml heparin column. Flow through contained 77% and B wash contained 16% of the applied EPI activity. No EPI was detected in eluates with 0.25, 0.75 and 1.5M NaCl respectively.

(Asp1-Thr161)-EPI (SEQ ID NO: 7) has one potential N-linked glycosylation site (Asn117) and the importance of this glycosylation for activity was investigated.

(Asp1-Thr161)-EPI (SEQ ID NO: 7) was purified from COS culture medium by affinity chromatography of FXa-Sepharose. In SDS-PAGE the purified protein appeared as a glycosylated band near 27 kDa and an unglycosylated band near 22 kDa (shown by treatment with endogylcosidase F). The glycosylated and unglycosylated forms were separated in unreduced SDS-PAGE and were extracted from the gel. Both forms were active in the EPI assay and showed the same specific activity as judged from the staining intensities in the SDS-gel. Glycosylation at Asn117 is therefore apparently not essential for EPI activity and active (Asp1-Thr161)-EPI (SEQ ID NO: 7) can thus be obtained in efficient expression systems where mammalian N-linked glycosylation is not obtained, e.g. in procaryots, or as unsecreted protein in yeast.

We claim:

1. An analogue of extrinsic pathway inhibitor (EPI) which analogue is a derivative of the full-length EPI sequence depicted in SEQ ID NO: 1, and which analogue retains the anticoagulant activity of native EPI as well as anti-FXa activity, comprises the three Kunitz protease inhibitor domains present in EPI, but has a heparin binding capacity less than 50% of the heparin binding capacity of native EPI when each is contacted with immobilized heparin under physiological conditions.

2. EPI analogue according to claim 1 comprising the amino acid sequence from Asp1 to Thr161 (SEQ ID NO: 7) of the native EPI molecule.

3. EPI analogue according to claim 1 comprising the amino acid sequence from Glu15 to Thr161 (SEQ ID NO: 5) of the native EPI molecule.

4. EPI analogue according to claim 1 and further having a Ser as the N-terminal amino acid residue.

5. DNA-sequence encoding an EPI analogue according to claim 1.

6. Expression vector containing a DNA-sequence according to claim 5.

7. Transformed or transfected microorganism or cell line comprising a vector according to claim 6.

8. A method for preparation of an EPI analogue wherein a microorganism or cell line according to claim 7 is cultured in a suitable culture medium and said EPI analogue is isolated therefrom.

9. A therapeutic preparation comprising an EPI analogue according to claim 1 and a suitable adjuvant or carrier.

* * * * *